United States Patent [19]

Winkler

[11] Patent Number: 4,779,619

[45] Date of Patent: Oct. 25, 1988

[54] $^{23}$NA MAGNETIC RESONANCE FUNCTIONAL BRAIN IMAGING

[75] Inventor: Stefan S. Winkler, Madison, Wis.

[73] Assignee: Wisconsin Alumni Research Foundation, Madison, Wis.

[21] Appl. No.: 896,945

[22] Filed: Aug. 15, 1986

[51] Int. Cl.$^4$ .................................... A61B 5/05
[52] U.S. Cl. ..................................... 128/653
[58] Field of Search ............... 128/653, 654, 659, 635; 324/309, 306

[56] References Cited

U.S. PATENT DOCUMENTS

| | | | |
|---|---|---|---|
| 4,398,213 | 8/1983 | Haendle et al. | 358/111 |
| 4,523,596 | 6/1985 | Macouski | 128/653 |
| 4,615,340 | 10/1986 | Cronenberg et al. | 128/635 |
| 4,635,643 | 1/1987 | Brown | 128/653 |
| 4,637,400 | 1/1987 | Marcus | 128/653 |

OTHER PUBLICATIONS

Powers et al., "Positron Emission Tomography and its Application to the Study of Cerebrovascular Disease in Man", Stroke, 16:3 pp. 361-376, May-Jun. 1985.
Halbach et al., "Techniques for Measurement of Regional Cerebral Blood Flow Using NMR", IEEE 1981 Frontiers of Engineering in Health Care, pp. 159-162.
Winkler et al., "Functional Brain Imaging with $^{23}$Na MRI using Change of Regional Cerebral Na (rCNa) as an Index", Soc. of Magnetic Resonance in Medicine, Abstracts, Aug. 19-23, 1985.
Hilal et al., "In Vivo NMR Imaging of Sodium-23 in the Human Head" Jour. of Computer Assisted Tomography, 9(1):1-7, Jan. 1985.
DeLayre et al., "Gated Sodium-23 Nuclear Magnetic Resonance Images of an Isolated Perfused Working Rat Heart", Science, vol. 212, May 1981.
Winkler et al., "Xenon Inhalation as an Adjunct to Computerized Tomography of the Brain: Preliminary Study", Investigative Radiology, 12:1 pp. 15-17, Jan.-Feb. 1977.

Primary Examiner—Ruth S. Smith
Attorney, Agent, or Firm—Lathrop & Clark

[57] ABSTRACT

Magnetic resonance imaging of sodium levels in the brain is used as a method for determining regional brain function. Direct measurement of sodium levels can be directly used to determine characteristics of blood volume in the cerebrum for research, diagnostic or clinical applications. Determination of the ratio between changes in sodium level changes and changes in arterial dissolved carbon dioxide levels can be used as a measure of regional vascular reserve when compared with norms, as an early indicator of possible cerebral ischemia. Grey scale images can be made by tomographic methods of the information generated by these scans.

9 Claims, No Drawings

$^{23}$NA MAGNETIC RESONANCE FUNCTIONAL BRAIN IMAGING

FIELD OF THE INVENTION

The present invention relates to the general field of diagnostic imaging of the internal structure or functioning of the human or animal body in general, and relates, in particular, to non-invasive imaging of the human brain for diagnostic or investigational purposes.

BACKGROUND OF THE INVENTION

There are now several technologies available for non-invasive imaging of the internal structure of the human body. These technologies include computerized tomography (CT), positron emission tomography (PET), and magnetic resonance imaging (MRI). These various broad approaches have advantages and disadvantages for imaging any particular portion or function of the body and variations on each technique have been found useful for particular applications or for imaging of particular bodily functions.

Imaging directed toward determining regional brain function can be conducted under present technology by several variations of these methods. The principle technique used to measure regional brain function is to measure regional cerebral blood flow (rCBF), which is most commonly measured at present by injection or inhalation of an inert diffusable tracer which can be followed by radionuclide or other detector systems. Recently introduced tomographic techniques give decidedly better information. CT, utilizing stable xenon as a tracer, PET scanning, and single photon emission computerized tomography (SPECT) are all tomographic techiques for brain imaging that have both particular advantages and particular limitations. PET is a quite powerful imaging device that can measure rCBF, regional cerebral blood volume (rCBV), and oxygen consumption and extraction, thereby giving a rather complete picture of cerebral metabolism which can be imaged regionally. Certain isotopes are available which also allow for regional glucose metabolism and neurotransmitter function to be measured. However the isotopes for use in PET scanning tend to be short lived and must often be produced by a nearby dedicated cyclotron with facilities for nuclear chemistry. Therefore the application of PET technology in clinical environments has been somewhat limited. SPECT does allow for tomographic evaluation of rCBF without dependence on a nearby cyclotron for isotopes, but the resulting image has relatively poor spatial resolution. Serial transmission CT using stable xenon as a tracer does provide rCBF determination with appropriate definition and has good spatial resolution. While such CT scanning can be widely used clinically, since access to a CT scanner is the principle need, it is not strictly a tracer method since the xenon must be given to the patient in pharmacologic doses that themselves effect brain metabolism.

Therefore all existing methodologies of measuring cerebral function have significant limitations. A hypothetical ideal method would be one that is not invasive, is rapid, can be tomographic in any desired plane, does not require tracers or pharmacologic agents, does not require radiation, and should be relatively inexpensive, so that it can be performed on readily available imaging equipment. The present invention is intended to satisfy many of these objectives.

Magnetic resonance imaging is most typically directed toward imaging of protons. Proton MRI has been very successful in defining anatomy and flow in blood vessels although as yet it has not yielded any data for studying tissue metabolism and perfusion. MRI equipment suitable for use in proton imaging can also be used to image sodium, in its most abundant naturally occurring isotope $^{23}$Na. $^{23}$Na is second only to protons from the standpoint of both natural abundance in the body and magnetic resonance imaging characteristics. It has been known before that sodium can be imaged using MRI techniques, but there have not been significant proposals for functional brain imaging with sodium scanning.

SUMMARY OF THE INVENTION

The present invention is summarized in that an image of regional brain function is made by magnetic resonance imaging of $^{23}$Na so as to gain a measure of cerebral blood volume to provide indications of regional cerebral function.

It is another object of the present invention to provide a method of creating an index of regional cerebral vascular reserve as a possible indication of impending brain ischemia.

It is another object of the present invention to provide a non-invasive methodology for tomographic imaging of brain function without the need for tracer materials, pharmacologic agents or radio active materials.

It is a further object of the present invention to provide such a methodology that can be widely used in clinical situations on existing or readily available equipment.

It is an advantage of the present invention in that it provides an additional clinical and diagnostic tool to clinicians handling patients with potential cerebral vascular problems or deficiencies.

Other objects, advantages and features of the present invention will become apparent from the following specification.

DESCRIPTION OF THE INVENTION

In summary, the present invention is directed toward testing and imaging of regional brain function by utilizing magnetic resonance imaging of $^{23}$Na naturally present in the brain of the patient. Imaging for sodium yields useful information since sodium is distributed in the cerebral space differentially. Most brain sodium is located in the interstitial space in the brain cavity. In spite of the fact that the intracellular volume of cranial capacity far exceeds the interstitial space, twice as much sodium in the brain exists in the interstitial space as in the intracellular spaces. In addition, it is estimated that perhaps as much as 60% of the intracellular sodium undergoes very rapid $T_2$ relaxation and is therefore relatively invisible to MRI. Therefore in considering effective visibility of cranial sodium to MRI scanning, it is estimated that approximately 74% of visible $^{23}$Na is in interstitial space while effectively 13% is dedicated respectively to intracellular and intravascular areas of cerebral volume. Thus most of the sodium signal of the brain will originate in cells interstitial space, blood and cerebrospinal fluid. The published and known relationship of change in rCBV per unit change in partial pressure of $CO_2$, ($PaCO_2$) can be used to derive change in regional cerebral sodium (rCNa) per unit change of $PaCO_2$ using published and known values of serum sodium, cerebral hematocrit (0.75-0.85 times large vessel hematocrit) interstitial fluid volume and intra and extracellular sodium concentrations. In the normal, changes in rCBF are accompanied by changes in rCBV, and it is therefore possible to determine rCBV and relative flow in normals by measuring rCNa. This information can be measured in increments, calculated on a regional level, and mapped onto displays to create brain images. By using a base line, introducing an experimental variable, and then taking a change measurement of rCNa, it is possible to determine what changes in rCBV are caused by the variable by directly measuring rCNa. In this way regional brain function can be directly observed. It is also possible to take a single base-line image of the $^{23}$Na level over the entire cerebrum to discover regional disparities or differing relative blood availability in the brain.

One of the other important attributes which can be measured in brain function using this technique is the regional vascular reserve of the brain of the patient. Depletion of regional vascular reserve can be a very sensitive and early indication of impending brain ischemia. The methodology for imaging of $^{23}$Na in the brain as disclosed herein can provide an index of this regional vascular reserve. This can be done because it has been previously demonstrated that the ratio in the change of rCBV to the change, of arterial partial pressure of carbon dioxide ($PaCO_2$) can serve as such an index. Since it has been demonstrated that as a patient breaths carbon dioxide, regional cerebral sodium (rCNa) increases in proportion to rCBV, measurement directly of rCNa and the $PaCO_2$ will serve as the index of regional vascular reserve since change in rCNa is proportional to rCBV. The steps in creating this index are as follows:

The first step in performing the measurement of vascular reserve is to obtain a base index scan of Na$^{23}$ by magnetic resonance. The next step is to repeat the $^{23}$Na scan while the patient is continuously inhaling a mixture of 95% oxygen and 5% carbon dioxide, while at the same time measuring either end tidal carbon dioxide continuously or $PaCO_2$ intermittently. Based on the data obtained by these measurements, it is then possible to calculate what the ratio of the change of rCNa to the change in $PaCO_2$ is regionally for the patient. This data can then be compared with the normal value for the patient's age, sex, blood pressure, hematocrit and serum sodium values. The steps of calculating the ratio and doing this comparison can be performed by a computer program, also the resultant values can be displayed on a grey scale image map which will thus give a regional map of vascular reserve. Such a vascular reserve map can be created in tomographic form giving, in essence, a cross-sectional view that is a regional map of vascular reserve left to the patients. Such a map, if taken of a patient in suspect condition, can be an early indication of impending brain ischemia and thus of great clinical interest.

This imaging will be done on a conventional nuclear magnetic resonance scanner specifically set up for sodium scanning. It is an understood variable of such a system that the contrast obtainable from the image is directly proportional to the static magnetic field of the scanner itself. In addition, the contrast is proportional to the square root of the imaging time, so that the length of the imaging time can affect the detail of the resulting image. For clinical purposes imaging times beyond thirty minutes are probably not practical. It has previously been determined by others that the expected relationship, i.e. that the contrast is inversely proportional to the object diameter, holds true for Na$^{23}$ magnetic resonance scanning. By extrapolating the data available for a 1.5 Tesla system, it has been calculated that the voxel size needed to detect a 10 mmHg change of $PaCo_2$ is about 2 cubic centimeters. A change in $PaCo_2$ of this level will cause an increase of 0.7 meq/L in regional sodium or a 25% increase in rCBV, using calculations from the literature. This is sufficient contrast in order to make a generalized regional determination of regional brain function, even though the resolution is not the optimum that might be clinically desired. The resolution can be significantly increased by increases in magnetic field strength by increasing scan time, or by further refinement of the process and procedure disclosed here.

EXPERIMENTAL EXAMPLE

A 10 kilogram rhesus monkey was anaesthetized with ketamine, intubated, and placed on a pump respirator. The animal was placed in a 1.5 Tesla General Electric magnetic resonance scanning system. The scanning system was set up with a 20 centimeter diameter head coil and a preamplifier assembly operating at 16.89 megahertz. Scan times were twenty minutes.

A base line control $^{23}$Na scan was first performed with the animal breathing room air at 1.25 respirations per minute. The respiratory gases to the animal were then switched to 5% carbon dioxide and 95% oxygen and a second magnetic resonance scan was performed. Finally a third scan was obtained with the animal hyperventilating room air at 3.75 respirations per minute. All scan created grey-scale images of $^{23}$Na presence. Arterial blood samples for blood gas and pH analysis were obtained through a femoral artery catheter inserted at the beginning of the procedure. Serium sodium and hematocrit levels were determined through a venous sample before the procedure. The partial pressure of oxygen was above 100 mmHg throughout the experiment. The sodium magnetic resonance scan were obtained using a 2-D spin warp sequence having a TE=10 msec, TR=133 msec, NAV=50, slice thickness equal 2 cm, and an X and Y spatial resolution=3.8 mm. Resulting image had a voxel size of 0.29 cm$^3$. Serum sodium in the animal was found to be 146 meq/L, and hematocrit was 34.6.

A second experiment was performed on a similar animal using a 3-D image acquisition technique. The second experiment was similar to the first except that during the hypercapnia scan, the animal was given 10% rather than 5% carbon dioxide to inhale, and during the third scan the animal was not hyperventilated, but was returned to a state of normal venilation. Imaging time for each scan was thirty minutes and the slice thickness was 1 centimeter rather than 2 centimeters. In plane resolution was 3 mm.

The region of interest image in each of the two scans included nearly the entire brain on either side of the mid-line of a mid-coronal section. The region of interest was 2.2 cm$^3$ in the first experiment and 1.1 cm$^3$ in the second experiment. The region of interest box was poiitioned to give a minimum signal and a minimum standard deviation reading in order to obtain as homogeneous a sample as possible and avoid cerebral spinal fluid and venous space as much as possible. The higher signal readings with greater standard deviations in the first experiment are due to the greater slice thickness and the inclusion of more cerebral spinal fluid and venous structure within the region of interest. The difference between the hypercapnia experiment controls before and after hypercapnia are significant because the change was seen for both sides of the brain in two separate experiments. The results of these tests can be tabulated as follows:

TABLE I

| | | | SIGNAL STRENGTH | | Estimated Brain Na (meq/L) | rCNa PaCO$_2$ (meq/100 g/Torr) |
|---|---|---|---|---|---|---|
| Condition | PaCo$_2$ | pH | Right Side | Left Side | | |
| First Animal | | | | | | |
| Resting | 36 | 7.48 | 1202 ± 229 | 1249 ± 382 | 53 | 33 × 10$^{-3}$ |
| 5% CO$_2$ | 63 | 7.27 | 1299 ± 212 | 1418 ± 361 | 64 | |
| Hyper-ventilate | 24 | 7.63 | 1205 ± 241 | 1162 ± 361 | 54 | |
| Second Animal | | | | | | |
| Resting | 43.8 | 7.29 | 557 ± 85 | 414 ± 48 | 46 | 20 × 10$^{-3}$ |
| 10% CO$_2$ | 97.3 | 7.03 | 616 ± 83 | 625 ± 53 | 57 | |
| Resting | 51.6 | 7.25 | 584 ± 78 | 535 ± 70 | 52 | |

The estimated brain sodium (next to last column in the above table) was approximated by assuming a direct proportion between signal strength and sodium concentration and assuming that the cerebral spinal fluid concentration was 146 meq/L, or the same as the serum level in the animal. These observations support the hypothesis that change in cerebral blood volume is reflected by a change in the $^{23}$Na magnetic resonance image and thus indicate that the use of such an image is appropriate for measurements of cerebral blood volume in human patients.

In an in vitro experiment using whole blood it was determined that pH in the range of 7.0 to 7.8 does not affect the NMR spectrum or relaxation time of $^{23}$Na. Since this pH range far exceeds normal physiologic range, and since there is no reason to believe that other tissues (including brain) would behave differently than blood, it may be concluded that pH will not independently affect the $^{23}$Na MRI image.

In this way it is possible to gain sensitive and early indication of regional vascular reserve by measuring indirectly regional cerebral blood volume by measuring directly regional cerebral sodium levels. This can be accomplished by magnetic resonance on existing machinery with significant major advantages over radioisotope or computer tomographic methods. These advantages include that there is no radiation to the subject and there is no need for cyclotron to create isotopes for introduction to the patient. In addition because there is no decay product or washout, the examination can be readily repeated without delay. It is further expected that the resolution will increase as the technique is further refined and enhanced. The method logy is superior to current methods of calculating rCBV data which rely principally on detecting assymmetry of blood distribution. A bilateral decrease in regional blood volume is not readily detectable by previously existing methods but is easily detectable by the method disclosed here when the results are compared with appropriate norms.

It is to be expressly understood that the foregoing example is for illustration only and is not to be limiting, but that the present invention is more properly defined by the scope of the following claims.

I claim:

1. A method of monitoring changes in regional cerebral blood volume in a patient comprising the steps of measuring $^{23}$Na changes in the patient's cerebrum by a magnetic resonance scanning and using the measured changes as an indication of changes in regional cerebral blood volume.

2. A method as claimed in claim 1 wherein the $^{23}$Na level is monitored as CO$_2$ is introduced into the patient's respiratory gases.

3. A method as claimed in claim 2 further including the step of simultaneously testing the dissolved CO$_2$ level in the patient's blood.

4. A method as claimed in claim 1 further including creating a grey-scale image wherein each voxel is shaded by a grey scale value proportional to the difference between measured $^{23}$Na levels.

5. A method as claimed in claim 1 further including comparing the measured $^{23}$Na levels to norms developed for the patient's age, sex, blood pressure, hematocrit and serum sodium values to determine relative regional brain function.

6. A method of testing for regional vascular reserve in a patient's cerebrum comprising the steps of
conducting a first magnetic resonance scan of $^{23}$Na in the patient's cerebrum to obtain baseline $^{23}$Na information;
introducing a physiologically significant level of carbon dioxide into the patient's respiratory gases;
conducting a second magnetic resonance scan of $^{23}$Na in the patient's cerebrum;
simultaneously monitoring the level of dissolved carbon dioxide in the patient's blood; and
calculating the ratio of change in scanned $^{23}$Na level to the change in blood carbon dioxide level caused by the carbon dioxide in the respiratory gases as an index of regional vascular reserve.

7. A method as claimed in claim 6 further including displaying the ratios derived on a grey scale for each voxel of brain scan area to create a pictorial image of regional vascular reserve.

8. A method as claimed in claim 6 wherein the level of carbon dioxide is between about 5% and 10% of inspired respiratory gases.

9. A method as claimed in claim 6 further including comparing the calculated ratio to norms developed for the patient's age, sex, blood pressure, hematocrit, and serum sodium values to determine relative regional vascular reserve.

* * * * *